(12) United States Patent
Piantoni et al.

(10) Patent No.: US 9,913,760 B2
(45) Date of Patent: Mar. 13, 2018

(54) UNIT FOR MAKING ABSORBENT PADS FOR NAPPIES

(71) Applicant: GDM S.p.A., Bologna (IT)

(72) Inventors: Matteo Piantoni, Albino (Bergamo) (IT); Valerio Soli, Bologna (IT)

(73) Assignee: GDM S.P.A., Bologna (IT)

( * ) Notice: Subject to any disclaimer, the term of this patent is extended or adjusted under 35 U.S.C. 154(b) by 6 days.

(21) Appl. No.: 14/772,706

(22) PCT Filed: Apr. 8, 2014

(86) PCT No.: PCT/IB2014/060515
§ 371 (c)(1),
(2) Date: Sep. 3, 2015

(87) PCT Pub. No.: WO2014/170794
PCT Pub. Date: Oct. 23, 2014

(65) Prior Publication Data
US 2016/0008180 A1  Jan. 14, 2016

(30) Foreign Application Priority Data

Apr. 17, 2013  (IT) .............................. BO2013A0171

(51) Int. Cl.
*A61F 13/15*  (2006.01)

(52) U.S. Cl.
CPC .. *A61F 13/15626* (2013.01); *A61F 13/15617* (2013.01); *A61F 13/15764* (2013.01)

(58) Field of Classification Search
CPC .......... A61F 13/15626; A61F 13/15764; A61F 13/15617
See application file for complete search history.

(56) References Cited

U.S. PATENT DOCUMENTS 4,908,175 A    3/1990 Angstadt
5,161,283 A *  11/1992 Hansen ............. A61F 13/15626
                                                            19/148

(Continued)

FOREIGN PATENT DOCUMENTS

EP    2308432 A1    4/2011
EP    2308433 A1    4/2011

(Continued)

OTHER PUBLICATIONS

International Search Report dated Jun. 4, 2014 from counterpart App No. PCT/IB2014/060515.

*Primary Examiner* — Robert B Davis
(74) *Attorney, Agent, or Firm* — Shuttleworth & Ingersoll, PLC; Timothy J. Klima

(57) ABSTRACT

A unit for making absorbent pads for nappies including a forming drum by which the absorbent pad is formed and in turn including on its peripheral surface one or more suction recesses; at least one hood for feeding the absorbent material and peripherally facing at least part of the peripheral surface of the drum; and a duct which leads to the hood and which can intermittently feed predetermined charges of a superabsorbent material; the feeding duct is configured in such a way that the flow of superabsorbent material fed into the hood expands until reaching an extent corresponding to the longitudinal extension of the at least one discrete layer of the absorbent pad.

16 Claims, 4 Drawing Sheets

(56) References Cited

U.S. PATENT DOCUMENTS

| | | | | |
|---|---|---|---|---|
| 5,245,728 A | * | 9/1993 | Rupp | D01G 23/02 19/148 |
| 5,447,677 A | * | 9/1995 | Griffoul | A61F 13/15658 264/113 |
| 7,244,387 B2 | * | 7/2007 | Larsson | D04H 1/732 264/113 |
| 7,745,687 B2 | * | 6/2010 | Heyn | A61F 13/15626 604/367 |
| 9,060,898 B2 | | 6/2015 | Hoshika | |

FOREIGN PATENT DOCUMENTS

| | | | |
|---|---|---|---|
| JP | 2009112347 A | * | 5/2009 |
| WO | WO2012105443 A1 | | 8/2012 |

* cited by examiner

UNIT FOR MAKING ABSORBENT PADS FOR NAPPIES

This application is the National Phase of International Application PCT/IB2014/060515 filed Apr. 8, 2014 which designated the U.S. and that International Application was published under PCT Article 21(2) in English.

This application claims priority to Italian Patent Application No. BO2013A000171 filed Apr. 17, 2013, which application is incorporated by reference herein.

TECHNICAL FIELD

This invention relates to a unit for making absorbent pads for nappies.

BACKGROUND ART

Typically, nappies comprise an impermeable layer, for example of polyethylene, a layer of non-woven fabric permeable to liquids and an absorbent pad sandwiched therebetween.

Nappies also comprise a liquid acquisition layer interposed between the absorbent pad and the permeable layer of non-woven fabric in order to promote liquid distribution in the absorbent pad.

Absorbent pads are made mainly from natural fibre particles (known as "fluff") uniformly blended with particles of superabsorbent polymer material ("SAP").

In recent years, higher pad absorption capacity has been achieved by absorbent pads comprising one or more discrete absorbent layers made mainly from particles of superabsorbent polymer material ("SAP").

Known from the prior art is a unit for making absorbent pads for nappies and comprising a drum, which rotates about its axis of rotation and which has on its peripheral cylindrical surface a plurality of suction housings or recesses within which respective absorbent pads are formed.

The unit also comprises a hood for feeding the particles of fluff mixed with the particles of "SAP" and which is mounted along a stretch of predetermined width above the peripheral cylindrical surface and the corresponding suction recesses.

Once a suction recess on the drum has been filled with fluff mixed with the "SAP", fed by the hood, a respective finished absorbent pad is obtained.

During the formation of the absorbent pads in the suction recesses, the feeding duct intermittently feeds the "SAP" directly into the suction recesses on the drum, thus defining the above mentioned discrete absorbent layers.

It has been found, however, that the "SAP" fed into the suction recesses does not settle on top of the mixture of fluff and "SAP" already present in each suction recess but penetrates into it, thus spoiling the absorbent pad being formed and negatively affecting the quality of the finished absorbent pads.

Aim of the Invention

This invention has for an aim to provide a unit for making absorbent pads for nappies and which overcomes the above mentioned disadvantages of the prior art.

BRIEF DESCRIPTION OF THE DRAWINGS

The invention will now be described with reference to the accompanying drawings which illustrate a non-limiting embodiment of it and in which.

DETAILED DESCRIPTION OF PREFERRED EMBODIMENTS OF THE INVENTION

Figure 1:
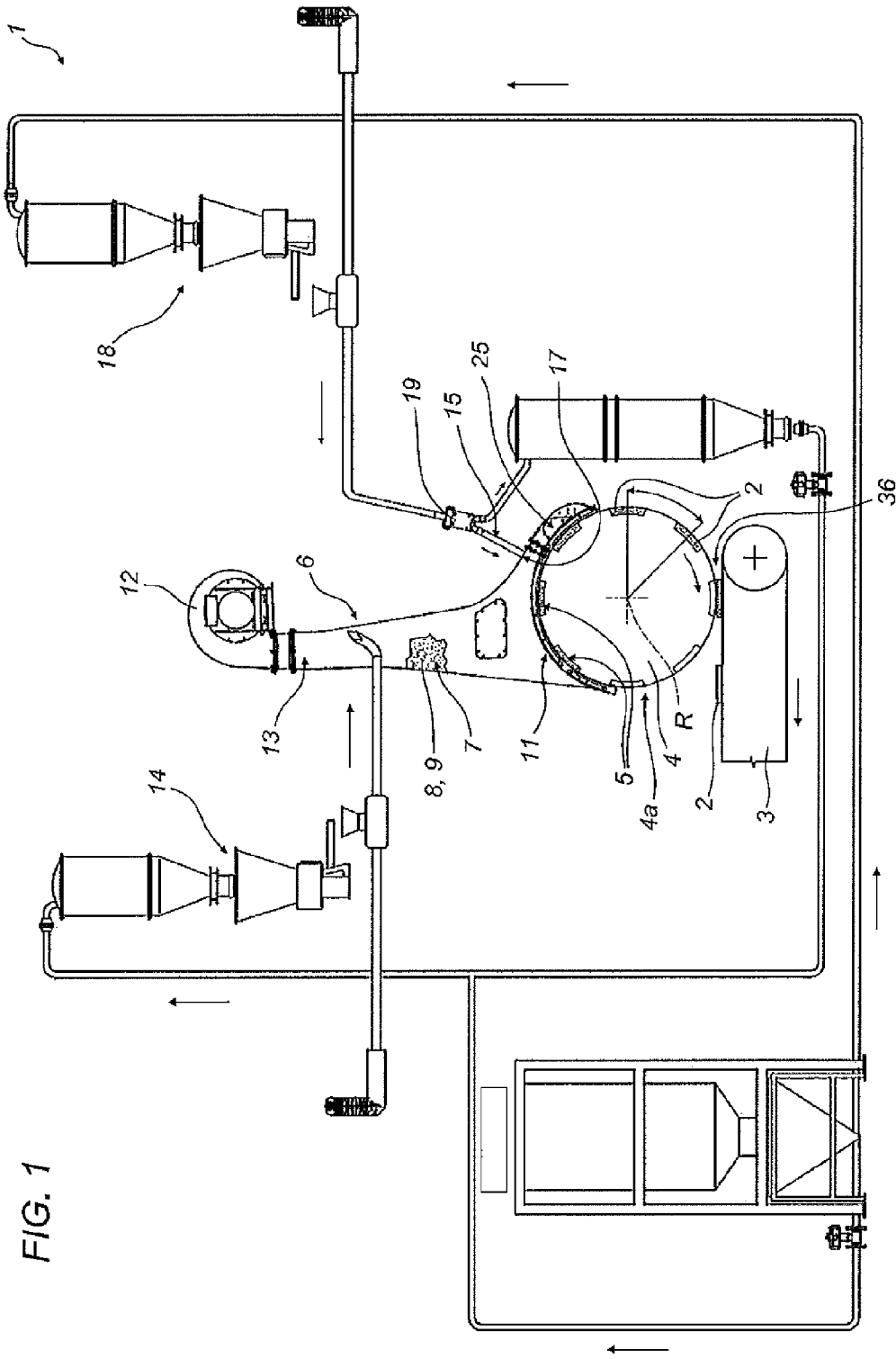
FIG. 1 is a schematic front view illustrating a unit for making absorbent pads for nappies according to this invention.

With reference to FIG. 1, the numeral 1 denotes in its entirety a unit for making absorbent pads 2 for nappies.

Generally speaking, a nappy comprises a sheet of permeable material and a sheet of impermeable material having, sandwiched between them, an absorbent pad 2 constituting the part of the nappy whose function is to absorb liquids.

For this purpose, the absorbent pad 2 is made mostly of natural fibre material (fluff) 8 uniformly blended with superabsorbent polymer material ("SAP") 9.

Preferably, the superabsorbent material used is superabsorbent polymer material in granular form.

Also, to increase its absorbent capacity, the pad 2 comprises a discrete absorbent layer made mainly from superabsorbent polymer material ("SAP") 9.

The unit 1 comprises a feed line 3 along which the finished absorbent pads 2 are fed.

The unit 1 comprises a forming drum 4 by which the absorbent pads 2 are formed.

The drum 4 is substantially tangent to the feed line 3 at a release station 36.

The drum 4 has a horizontal axis of rotation R perpendicular to the feed line 3.

More specifically, as illustrated in FIG. 1, the drum 4 rotates about its axis R in a clockwise direction.

The drum 4 has a peripheral cylindrical surface 4a with at least one suction recess 5 formed thereon.

In the embodiment illustrated, the peripheral surface 4a has a plurality of suction recesses 5 angularly distributed along its surface of revolution.

The suction recesses 5 are located on the peripheral surface 4a of the drum 4 at a predetermined spacing P.

The unit 1 comprises a hood 6 for feeding at least one absorbent material 7 and peripherally facing the drum 4 for at least part of the peripheral surface 4a of the drum 4.

In the preferred embodiment, the hood 6 is located above the drum 4 and the drum 4 is interposed between the feed line 3 and the feeding hood 6.

Together with the drum 4, the hood 6 defines a closed chamber for forming the pads 2 inside the recesses 5.

The hood 6 is delimited by a front wall 21, a rear wall 22 and two flanks 23 and 24, or side walls, each of which connects the front wall 21 to the rear wall 22.

With reference to the direction of rotation of the drum 4, the flank labelled 24 is the left-hand flank and the flank labelled 23 is the right-hand flank of the hood 6.

In the preferred embodiment, the hood 6 comprises a protrusion 25 defining a lateral extension of the hood 6.

In a variant not illustrated, the hood 6 comprises two protrusions 25 or lateral extensions.

In a further variant not illustrated, the hood 6 does not have any protrusion 25.

More specifically, the lateral protrusion 25 extends along the peripheral surface 4a of the drum 4.

The protrusion 25 has an elongate shape and extends in a substantially circumferential direction.

The protrusion 25 is delimited by respective portions of the front wall 21, of the rear wall 22 and of one of the two flanks 23, 24 of the hood 6. In the preferred embodiment, the protrusion is delimited by a portion of the right-hand flank 23 of the hood 6.

The hood 6 has an inlet opening 13 and a feeding outlet 11 facing the peripheral surface 4a of the drum 4.

The inlet opening 13 is located at one of the ends of the hood 6, on the side opposite the feeding outlet 11.

The cross-sectional structure of the hood 6 is divergent in shape from the inlet opening 13 to the feeding outlet 11.

The hood 6 comprises a blower 12, located at the inlet opening 13, for supplying the fluff fibre material 8 under pressure.

The unit 1 comprises a first system 14 for metering and feeding the "SAP" 9.

The first system 14 feeds predetermined quantities of superabsorbent polymer material 9 into the hood 6.

The hood 6 comprises inside it a zone 10 for mixing and transporting the natural fibre material (fluff) 8 and the superabsorbent material "SAP" 9.

The first system 14 feeds predetermined quantities of superabsorbent polymer material 9 into the mixing and transporting zone 10 of the hood 6.

The charges of "SAP" 9 fed by the first system 14 into the mixing and transporting zone 10 of the hood 6 are proportional to the quantity of natural fibre material (fluff) 8 which is fed by the blower 12 and which is mixed therewith inside the hood 6.

The natural fibre material (fluff) 8 uniformly blended with the superabsorbent polymer material ("SAP") 9 defines the above mentioned absorbent material 7.

In an alternative embodiment, the absorbent material 7 comprises only natural fibre material (fluff) 8.

Since the fluff and the "SAP" are fed in the proximity of the inlet opening 13, their mixing, and the consequent formation of the absorbent material 7, occurs concurrently with their transportation towards the feeding outlet 11.

The feeding outlet 11 delivers the absorbent material 7, which settles in the suction recesses 5 of the drum 4 filling them gradually for as long as they are positioned to face the hood 6 following rotation of the drum 4.

With reference to the direction of rotation of the drum 4, once the peripheral surface 4a of the drum 4 facing the hood 6 moves out of the zone of action of the feeding outlet 11 of the hood 6, the suction recesses 5 house respective finished absorbent pads 2 which are released by the drum 4 to the feed line 3 at the release station 36.

In order to make in the absorbent pad 2 the above mentioned discrete absorbent layers, consisting mainly of the superabsorbent material "SAP" 9, the unit 1 comprises a duct 15 for feeding charges of "SAP" 9.

The duct 15 is located at the hood 6.

More specifically, the duct 15 leads to the hood 6.

In the preferred embodiment, the duct 15 leads to the protrusion 25.

By "leads to" is meant that the duct 15 preferably terminates at at least one of the walls of the hood 6 without extending further into the hood 6 itself. More precisely, it terminates at the right-hand flank 23 of the hood 6.

More specifically, the feeding duct 15 is solidly connected to the hood 6.

The feeding outlet 11 of the hood 6 feeds into the suction recesses 5 of the drum 4 the absorbent material 7, formed in the mixing and transporting zone 10, and the superabsorbent material "SAP" 9 delivered by the feeding duct 15.

For this purpose, the unit 1 comprises a second system 18 for metering and feeding superabsorbent material (SAP) 9 and comprising the feeding duct 15.

It should be noted that in the embodiment described, the superabsorbent material 9 metered and fed by the first and second systems 14 and 18 is the same.

Alternatively, the superabsorbent material 9 metered and fed by the first system 14 is different from that metered and fed by the second system 18.

The feeding duct 15 has an infeed end which is connected directly to valve means 19 for intermittently feeding the superabsorbent material and a delivery mouth 17 leading to the hood 6.

Preferably, the delivery mouth 17 is coplanar with one of the walls of the hood 6. More precisely, it is coplanar with the right-hand flank 23 of the hood 6.

The valve means 19 allow passing the "SAP" 9 into the feeding duct 15 intermittently, so that the feeding duct 15 feeds the "SAP" during the passage of each suction recess 5 of the drum 4 under the delivery mouth 17.

More precisely, the delivery mouth 17 faces the peripheral surface 4a of the drum 4.

According to the invention, the feeding duct 15 is configured in such a way that the flow of superabsorbent material 9 fed into the hood 6 expands until reaching an extent corresponding to the longitudinal extension of the at least one discrete layer of the absorbent pad 2.

Advantageously, the protrusion 25 defines a zone 26 for diffusing and expanding the superabsorbent material 9.

More precisely, the duct 15 for feeding the superabsorbent material 9 is configured in such a way that the superabsorbent material flows in at a first, inflow speed and out at a second, outflow speed lower than the first, inflow speed.

In other words, the feeding duct 15 has a divergent cross-sectional structure.

That means that an axisymmetric cross section of the duct 15 has a shape which diverges towards the hood 6.

Thus, the superabsorbent material 9 delivered by the feeding duct 15 settles in the suction recess 5 of the drum 4 without removing the absorbent material 7 accumulated therein previously.

The second, outflow speed at which the superabsorbent material 9 flows out of the feeding duct 15 is such as not to disturb the flow of the first absorbent material 7 transported towards the feeding outlet 11 inside the hood 6.

Advantageously, the feeding duct 15 has a defined length L of between 100 and 400 mm measured from the valve means 19 to the delivery mouth 17.

Preferably, the length L of the feeding duct 15 is 100 mm.

Advantageously, a relatively short feeding duct 15 allows making discrete layers of "SAP" 9 of defined and repeatable extension.

In order to correctly orient the superabsorbent material 9 flowing out of the feeding duct 15 relative to the suction recesses 5 of the drum 4, the feeding duct 15 extends mainly along a direction substantially at right angles to the peripheral cylindrical surface 4a of the drum 4.

One end of the protrusion 25 is in communication with the outside atmosphere, in particular through a grill 27 allowing air from the outside to flow inside.

Thus, the grill 27 allows air to flow from the outside atmosphere to the inside of the hood 6, thereby preventing the formation of unwanted vortices inside the diffusing and expanding zone 26.

In the preferred embodiment, the drum 4 comprises inside it a first, a second and a third suction chamber 28, 29 and 30, all facing the feeding outlet 11 of the hood 6.

The first, second and third chambers 28, 29 and 30 are located one after the other, in sequence, and the second chamber 29 is interposed between the first chamber and the third 28 and 30.

More specifically, the first chamber 28 faces the diffusing and expanding zone 26 and the second chamber 29 faces the mixing and transporting zone 10.

The third chamber 30 faces the mixing and transporting zone 10.

The chambers 28, 29 and 30 have respective partition walls 31, 32, 33, 34, at least one of the walls 32, 33 being in common with the respective adjacent chamber.

The first and second chambers 28 and 29 have a partition wall 32 in common. Advantageously, this partition wall extends radially.

Figure 3:
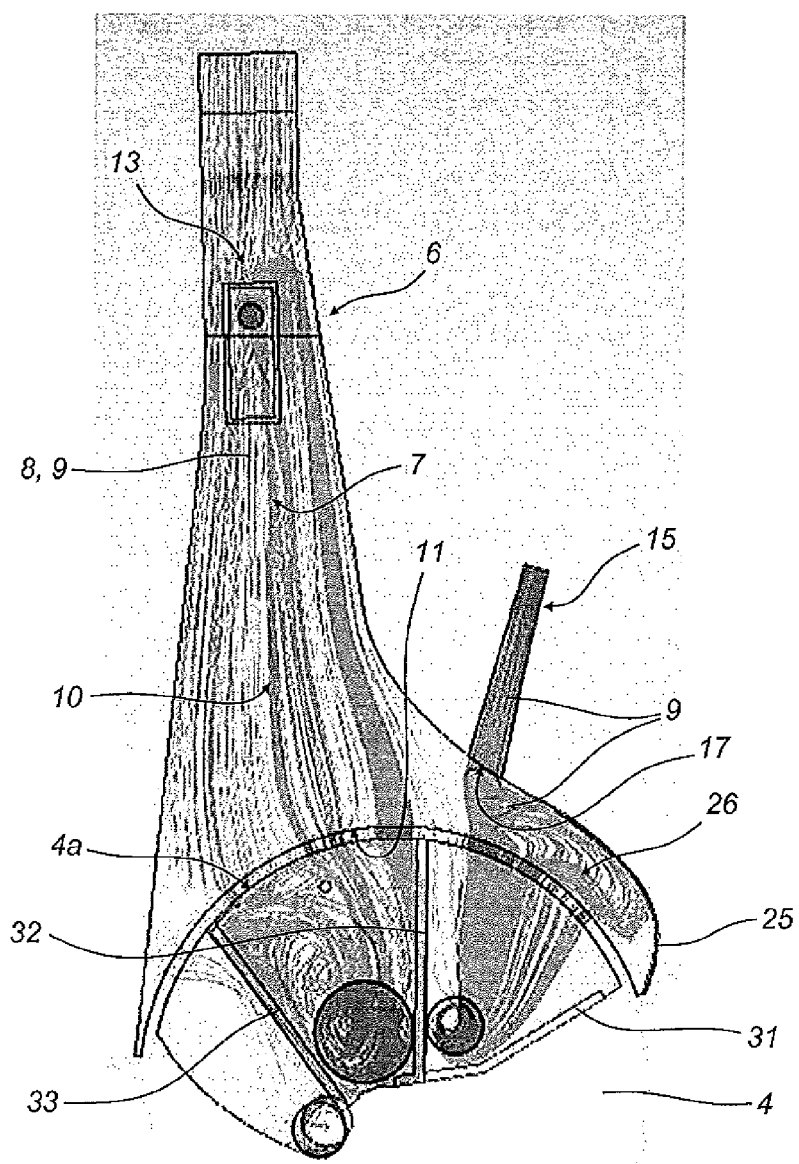
FIG. 3 illustrates the hood and the drum of FIG. 2, during operation.

This allows mainly conveying the flow of absorbent material 7 and the superabsorbent material "SAP" 9 from the feeding duct 15 respectively towards the first and second suction chambers 28 and 29 of the drum 4, as illustrated in FIG. 3.

It should be noted that the position of the feeding duct 15 affects the position of the discrete layers of absorbent material inside the absorbent pad 2.

Figure 2:
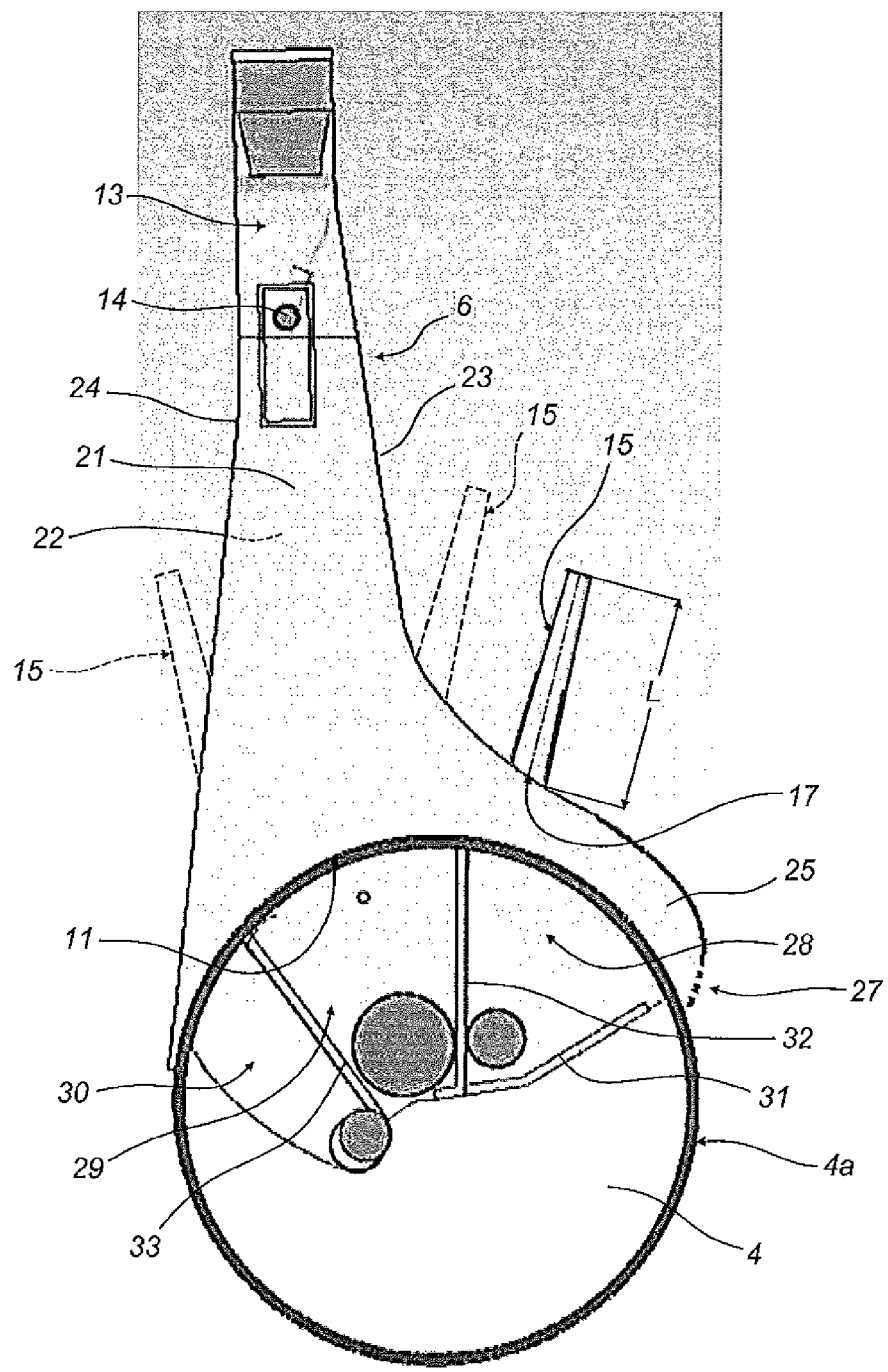
FIG. 2 is a scaled-up view, with some parts cut away in order to better illustrate others, showing a hood which feeds an absorbent material and a drum which forms absorbent pads, both the hood and the drum forming part of the unit of FIG. 1.

With reference to FIG. 2, the feeding duct 15 may be positioned upstream or downstream of the zone 10 for mixing and transporting the first absorbent material 7, according to the direction of rotation of the drum 4, in such a way as to deposit the superabsorbent material 9, defining the discrete layer of absorbent material, in the proximity of the bottom of the respective recess 5 of the drum 4.

In this case, the diffusing and expanding zone 26 is at least partly superposed on the mixing and transporting zone 10.

Alternatively, the diffusing and expanding zone 26 is defined by a protrusion 25 located upstream of the mixing zone 10, relative to the direction of rotation of the drum 4.

In order to deposit the discrete layers of superabsorbent material at an intermediate internal position of the absorbent pad 2, the feeding duct 15 must always be positioned closer to the zone 10 for mixing and transporting the absorbent material 7.

More specifically, as illustrated in FIG. 2, if the feeding duct 15 is positioned upstream of the protrusion 25 and leads to the zone 10 for mixing and transporting the absorbent material 7, the superabsorbent material 9 defining the discrete layer of absorbent material is deposited at an intermediate position of the recess 5 of the drum 4.

In this case, the diffusing and expanding zone 26 is at least partly superposed on the mixing and transporting zone 10.

In the preferred embodiment, since the feeding duct 15 is positioned at the protrusion 25, located downstream of the mixing zone 10 according to the direction of rotation of the drum 4, the superabsorbent material 9 defining the discrete layer of absorbent material is deposited on top of the absorbent material 7 already deposited in the recess 5 at the infeed end of the recess 5 itself.

It should be noted that since the drum 4 overturns the absorbent pads 2 along the feed line 3, the position of the discrete absorbent layers in the absorbent pad 2 advancing along the feed line 3 is upside down relative to their position inside the recesses 5 of the drum 4.

In order to deposit a plurality of discrete layers of superabsorbent material at the bottom of the recesses 5 of the drum 4 and at the infeed end of the recesses 5, the diffusing and expanding zone 26, defined by the protrusion 25, is located respectively upstream and downstream of the mixing zone 10, according to the direction of rotation of the drum 4.

Figure 4:
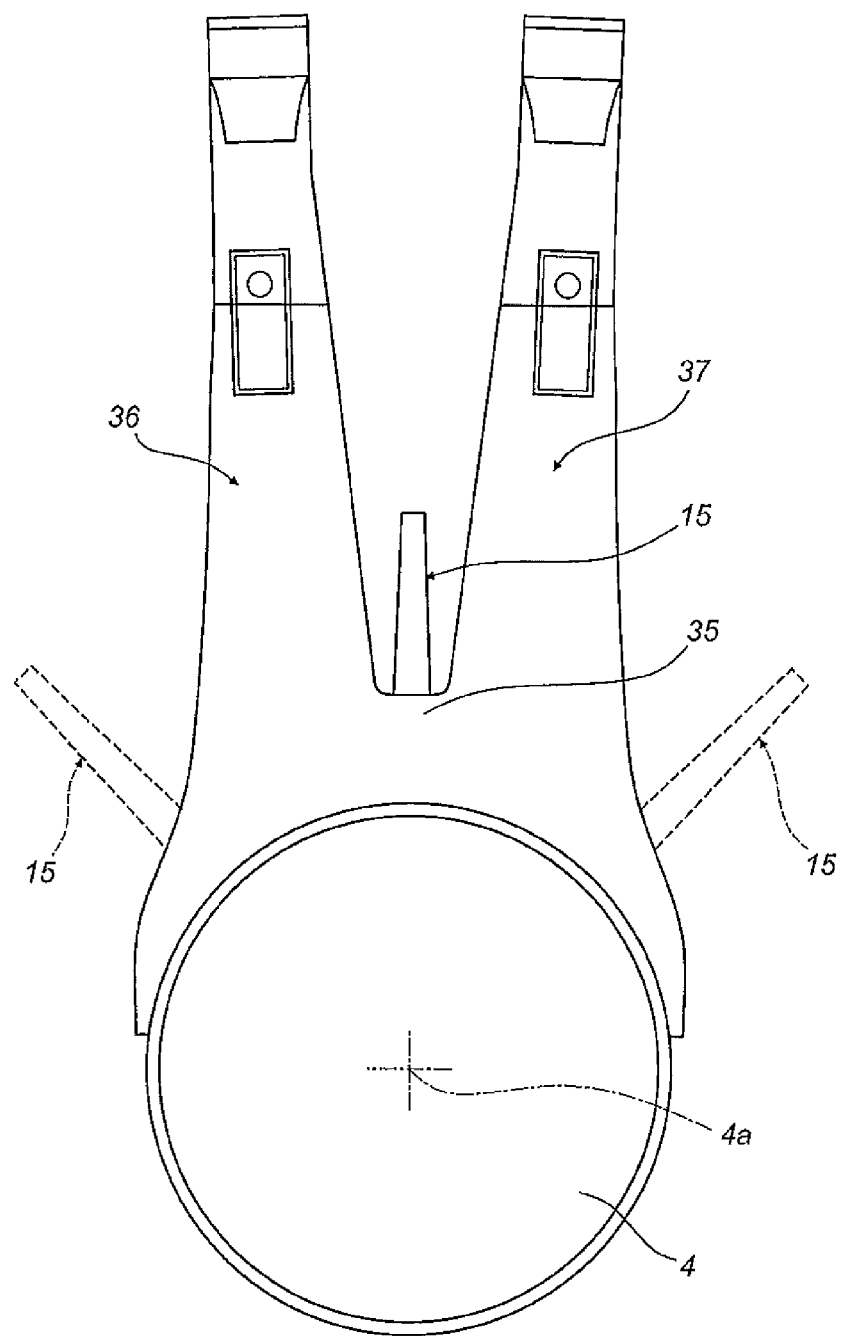
FIG. 4 is a schematic front view of an alternative embodiment of the unit according to this invention.

In an alternative embodiment illustrated in FIG. 4, the unit 1 comprises two hoods 6, in particular a first and a second hood 36 and 37, for feeding the absorbent material 7, mounted side by side, relative to the direction of rotation of the drum 4, and both facing the peripheral surface 4a of the drum 4.

In order to deposit discrete absorbent layers, made mainly of superabsorbent material, at least one of the two hoods comprises at least one feeding duct 15 associated therewith.

The two hoods 6 are in communication with each other by way of a connecting element 35 interposed between the two hoods 6 themselves.

It should be noted that in this embodiment, too, the feeding duct 15 may be positioned in different zones, relative to the first and second hoods 36 and 37, as a function of the position of the discrete layers of "SAP" in the absorbent pad 2.

More specifically, the feeding duct 15 may be located upstream and/or downstream of the first and second feeding hoods 36 and 37.

Lastly, this description also contemplates the use of two or more feeding ducts 15 to make two or more discrete layers of "SAP" in the absorbent pad 2.

According to this invention, the configuration of the feeding duct 15 and its position relative to the hood 6 allows expanding the flow of superabsorbent material until reaching an extent corresponding to the longitudinal extension of the at least one discrete layer, so that it settles in the recess 5 of the drum 4 of the absorbent pad without impacting the recess 5 at a speed such as to upset any absorbent material 7 already present in the suction recess 5 or such as to cause a backflow of the superabsorbent material 9 itself.

Advantageously, the spreading of the superabsorbent material 9 from the delivery mouth 17 of the feeding duct 15 to its settling on the respective drum recess 5 is also obtained by the combination of two or more of the above mentioned factors, such as, for example, the position of the feeding duct 15 relative to the hood 6 and to the drum 4, the cross-sectional structure of the duct 15 and the length of the feeding duct 15.

The invention claimed is:

1. A unit for making absorbent pads for nappies:
   wherein the absorbent pads each comprise an absorbent material and a discrete layer of superabsorbent material;
   the unit comprising:
   a forming drum by which the absorbent pad is formed, the forming drum including a peripheral surface and a suction recess on the peripheral surface;
   a hood for feeding the absorbent material and facing a portion of the peripheral surface of the forming drum;
   a first system for metering and feeding the superabsorbent material into the hood;
   a second system for metering and feeding the superabsorbent material, the second system for metering and feeding the superabsorbent material comprising a feeding duct for intermittently feeding predetermined charges of the superabsorbent material, the feeding duct leading to the hood;

wherein the feeding duct is configured such that a flow of superabsorbent material fed into the hood by the feeding duct expands until reaching an extent corresponding to a longitudinal extension of the discrete layer of superabsorbent material;

wherein the feeding duct is configured such that the superabsorbent material flows in at a first, inflow speed and out at a second, outflow speed lower than the first, inflow speed.

2. The unit according to claim 1, wherein the hood comprises a lateral protrusion extending along the peripheral surface of the forming drum; the feeding duct leading to the lateral protrusion of the hood.

3. The unit according to claim 1, wherein the feeding duct includes a divergent cross-sectional structure.

4. The unit according to claim 1, wherein the feeding duct includes an infeed end which is connected directly to a valve for intermittently feeding the superabsorbent material and a delivery mouth leading to the hood.

5. The unit according to claim 4, wherein the feeding duct has a defined length of between 100 and 400 mm measured from the valve to the delivery mouth.

6. The unit according to claim 1, wherein the forming drum comprises internally a first suction chamber and a second suction chamber having respective partition walls facing the hood.

7. The unit according to claim 6, wherein the first and second suction chambers have in common a partition wall which extends radially with respect to the forming drum.

8. The unit according to claim 1, wherein the hood comprises a first hood portion and a second hood portion which are mounted side by side with both facing the peripheral surface of the forming drum, the feeding duct being associated with at least one chosen from the first hood portion and the second hood portion.

9. The unit according to claim 1, wherein the feeding duct is solidly connected to the hood.

10. The unit according to claim 1, wherein the feeding duct is positioned substantially at right angles to the peripheral surface of the forming drum.

11. The unit according to claim 1, wherein the hood has a mixing and transporting zone for mixing and transporting the absorbent material; the feeding duct leading to the mixing and transporting zone.

12. The unit according to claim 11, wherein the protrusion defines a diffusing and expanding zone located at least one chosen from upstream and downstream of the mixing and transporting zone relative to a direction of rotation of the forming drum.

13. A unit for making absorbent pads for nappies:
wherein the absorbent pads each comprise an absorbent material and a discrete layer of superabsorbent material;
the unit comprising:
a forming drum by which the absorbent pad is formed, the forming drum including a peripheral surface and a suction recess on the peripheral surface;
a hood for feeding the absorbent material and facing a portion of the peripheral surface of the forming drum;
a feeding duct for intermittently feeding predetermined charges of the superabsorbent material, the feeding duct leading to the hood;
wherein the feeding duct is configured such that a flow of superabsorbent material fed into the hood expands until reaching an extent corresponding to a longitudinal extension of the discrete layer of superabsorbent material;
wherein the feeding duct is configured such that the superabsorbent material flows in at a first, inflow speed and out at a second, outflow speed lower than the first, inflow speed.

14. The unit according to claim 13, wherein the feeding duct includes a divergent cross-sectional structure.

15. A unit for making absorbent pads for nappies:
wherein the absorbent pads each comprise an absorbent material and a discrete layer of superabsorbent material;
the unit comprising:
a forming drum by which the absorbent pad is formed, the forming drum including a peripheral surface and a suction recess on the peripheral surface;
a hood for feeding the absorbent material and facing a portion of the peripheral surface of the forming drum;
a feeding duct for intermittently feeding predetermined charges of the superabsorbent material, the feeding duct leading to the hood;
wherein the feeding duct is configured such that a flow of superabsorbent material fed into the hood expands until reaching an extent corresponding to a longitudinal extension of the discrete layer of superabsorbent material;
wherein the feeding duct includes an infeed end which is connected directly to a valve for intermittently feeding the superabsorbent material and a delivery mouth leading to the hood.

16. The unit according to claim 15, wherein the feeding duct has a defined length of between 100 and 400 mm measured from the valve to the delivery mouth.

* * * * *